US007253142B1

(12) United States Patent
Suzuki et al.

(10) Patent No.: US 7,253,142 B1
(45) Date of Patent: Aug. 7, 2007

(54) PROTEIN SOLUTION PREPARATION AND METHOD OF STABILIZING THE SAME

(75) Inventors: Nobuyuki Suzuki, Tokyo (JP); Naoki Mitsui, Tokyo (JP); Takaya Hiraishi, Tokyo (JP); Yoshirou Watanabe, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/720,757

(22) PCT Filed: Sep. 8, 2000

(86) PCT No.: PCT/JP00/06144

§ 371 (c)(1), (2), (4) Date: Dec. 28, 2000

(87) PCT Pub. No.: WO01/17542

PCT Pub. Date: Mar. 15, 2001

(30) Foreign Application Priority Data

Aug. 9, 1999 (JP) ................................ 11-254896

(51) Int. Cl.
*A61K 38/16* (2006.01)

(52) U.S. Cl. ................ 514/2; 514/8; 514/12; 530/386; 530/380

(58) Field of Classification Search .................... 514/2, 514/8, 12; 604/181, 187, 207; 526/281; 222/386; 530/380
See application file for complete search history.

(56) References Cited

U.S. PATENT DOCUMENTS

| | | | | |
|---|---|---|---|---|
| 3,788,319 | A * | 1/1974 | Gillette | 604/7 |
| 4,732,889 | A | 3/1988 | Cynshi et al. | 514/8 |
| 4,810,249 | A * | 3/1989 | Haber et al. | 604/210 |
| 4,838,861 | A * | 6/1989 | Sharp | 604/6.01 |
| 4,992,419 | A | 2/1991 | Woog et al. | 514/8 |
| 5,004,460 | A * | 4/1991 | Gimeno | 604/228 |
| 5,213,814 | A * | 5/1993 | Goodrich et al. | 424/532 |
| 5,468,803 | A | 11/1995 | Takahashi et al. | 524/553 |
| 5,496,718 | A | 3/1996 | Hashimoto et al. | 435/232 |
| 5,534,269 | A | 7/1996 | Igari et al. | 424/489 |
| 5,571,788 | A | 11/1996 | Arvinte et al. | 514/12 |
| 5,651,966 | A * | 7/1997 | Read et al. | 424/93.72 |
| 5,661,125 | A | 8/1997 | Strickland | 514/8 |
| 5,728,437 | A | 3/1998 | Nygren et al. | 428/35.7 |
| 6,007,520 | A | 12/1999 | Sudo et al. | 604/181 |
| 6,046,274 | A | 4/2000 | Grandjean et al. | 525/92 A |

FOREIGN PATENT DOCUMENTS

| | | | |
|---|---|---|---|
| EP | 231819 | A2 | 8/1987 |
| EP | 490549 | A1 | 6/1992 |
| EP | 524802 | A1 | 1/1993 |
| EP | 556034 | A1 | 8/1993 |
| EP | 559146 | A1 | 9/1993 |
| EP | 576294 | A2 | 12/1993 |
| EP | 0 858 809 | | 8/1998 |
| EP | 0 879 611 | | 11/1998 |
| EP | 0 909 564 | | 4/1999 |
| EP | 1232753 | * | 8/2002 |
| GB | 2193631 | A | 2/1988 |
| JP | 2-96533 | * | 4/1990 |
| WO | WO 89/01791 | A1 | 3/1989 |
| WO | 96/38503 | | 12/1996 |
| WO | WO00/15241 | | 3/2000 |

OTHER PUBLICATIONS

Mou Steven S., New England Journal of Medicine 351 (16) 1635-44, 2004.*

Daikyo Technical Report, Apr. 1997, No. 974A063CG, pp. 1-12.

Derwent World Patents Index English Dialog Abstract corresponding to publication JP 54-135215 (JP Application No. 197841853).

English Patent Abstract of Japan Abstract corresponding to publication JP 11-146910 (JP Application No. 10-129579).

English Patent Abstract corresponding to publication JP 06-209992 (JP Application No. 5-293159).

English Patent Abstract of Japan Abstract corresponding to publication JP 2000-44487 (JP Application No. 11-149499).

English Patent Abstract of Japan Abstract corresponding to publication JP 62-000032 (JP Application No. 61-022930).

English Patent Abstract of Japan Abstract corresponding to publication JP 62-252731 (JP Application No. 62-0100398).

* cited by examiner

*Primary Examiner*—David Lukton
(74) *Attorney, Agent, or Firm*—Morgan & Finnegan, LLP

(57) ABSTRACT

The present invention provides stable protein solution formulations filled in a container made from a hydrophobic resin at least for the part in direct contact with said formulation.

10 Claims, No Drawings

PROTEIN SOLUTION PREPARATION AND METHOD OF STABILIZING THE SAME

This application is a 371 of PCT/JP00/06144, filed Sep. 8, 2000, which claims priority to Japanese application 254896/1999, filed Aug. 9, 1999.

FIELD OF THE INVENTION

The present invention relates to protein solution formulations which are easy to handle and stable over long periods. More specifically, the present invention relates to stable protein solution formulations prefilled in a resin container. The present invention also relates to methods for stabilizing protein solution formulations.

PRIOR ART

With the development of genetic recombination technology, various protein formulations are supplied in stable amounts. To ensure stability, these formulations are supplied in the dosage form of a lyophilized protein ingredient powder to be dissolved just before use in a water-soluble diluent, either separately packaged, or in the dosage form of a protein solution formulation containing additives which improve stability. When both dosage forms are compared, the solution dosage form is more advantageous in terms of convenience of use, but it is difficult to ensure its stability.

Usually, protein solution formulations are supplied to the market in a container such as a vial, ampule or disposable syringe containing active proteins together with diluents, solubilizing agents, isotonizing agents, excipients, pH-modifiers, buffers, sulfur-containing reducing agents, antioxidants or the like. Such a container should satisfy the following requirements: (1) it should keep protein formulations stable under long-term storage conditions; (2) it should be sufficiently resistant to heat and pressure in order to tolerate conditions employed in sterilization; (3) it should have chemical resistance; (4) container fragments should not enter solution formulations during use; (5) if the container is a syringe, its plunger should have good slidability; (6) it should have transparency to enable turbidity of the solution or contaminants to be detected; (7) it should be able to be transported easily; and (8) it should be resistant to leaching.

Glass containers are advantageous in terms of heat resistance, pressure resistance, chemical resistance and transparency, but involve complex and expensive processes such as coating of silicone or similar finishing agents and baking. Moreover, leaching from glass materials may cause drugs to become unstable or unsoluble matter to be produced. Glass containers are also inconvenient for transportation due to their weight and fragility.

Another problem with protein solution formulations is protein content loss caused by aggregation, denaturation or degradation, especially during long-term storage at room temperatures.

Therefore, there is a demand for development of protein solution formulations for long-term storage at room temperatures, but no formulations which satisfy all of the requirements described above have been developed, and no stable protein formulations prefilled in a resin container have yet been supplied to the market.

DISCLOSURE OF THE INVENTION

The inventors of the present invention examined reactivity between proteins and glass surfaces and reached the conclusion that polar residues originally present on glass material surfaces such as silanol or silyloxy might be primarily responsible for degradation and association of physiologically active proteins. Some means have been proposed and used to reduce the influence of these polar residues by, for example, coating polysilicone, alkylsilicone or the like on glass surfaces or by chemically masking silanol residues, but failed to essentially improve stability.

From the viewpoint of the affinity for container surfaces in contact with a protein solution particularly containing erythropoietin (EPO), the inventors hypothesized that when the normal phase of glass surfaces, i.e. stationary phase is filled with hydrophilic groups, hydrophilic residues of the protein would be highly distributed to the surfaces and that this may be lower stability. On the basis of this hypothesis, the inventors expected that if container surfaces had a reverse hydrophobic phase free from polar residues contrary to glass surfaces, distribution of fat-soluble residues of the protein would increase and polar residues of the protein responsible for degradation or association would be opposite to the container surfaces, thereby greatly contributing to improve stability of the protein.

The inventors also expected that the present invention would greatly contribute to improve stability of protein solution formulations having sugar chains, because such proteins tend to be readily adsorbed to containers.

The inventors found that stability of proteins can be ensured without container surface treatment by selecting a container having a hydrophobic, i.e. reverse phase. Namely, the inventors achieved the present invention on the basis of the finding that aggregation, denaturation and degradation can be inhibited to maintain a high protein content for a long period if protein solution formulations are filled in a resin container made from a specific material.

Accordingly, the present invention provides a stable protein solution formulation filled in a container made from a hydrophobic resin at least for the part in direct contact with said formulation.

The present invention provides said protein solution formulation wherein the container is made from a resin.

The present invention provides said protein solution formulation wherein the resin is selected from the group consisting of polyethylene, polypropylene, polyethylene terephthalate, polycarbonate, polyethyl methacrylate, and copolymers of these resins and cycloolefins.

The present invention provides said protein solution formulation wherein the resin is selected from ring-opened polymers of cycloolefins.

The present invention provides said protein solution formulation wherein the resin is selected from hydrogenated ring-opened polymers of cycloolefins.

The present invention provides said protein solution formulation wherein the ring-opened polymers of cycloolefins are ring-opened polymers of norbornene or tetracyclododecene.

The present invention provides said protein solution formulation wherein the hydrogenated ring-opened polymers of cycloolefins are hydrogenated ring-opened polymers of norbornene or tetracyclododecene.

The present invention provides said protein solution formulation wherein the resin is a cycloolefin copolymer consisting of a copolymer of a cyclic olefin and an olefin.

The present invention provides said protein solution formulation wherein the cycloolefin copolymer is a copolymer of norbornen or tetracyclododecene or a derivative thereof and ethylene or propylene.

The present invention provides said protein solution formulation wherein the cycloolefin copolymer is a copolymer of norbornene or tetracyclododecene and ethylene.

The present invention provides said protein solution formulation wherein the resin is a thermoplastic norbornene resin or a thermoplastic tetracyclododecene resin.

The present invention provides said protein solution formulation wherein the container is in the form selected from the group consisting of a vial, ampule, syringe and bottle.

The present invention provides said protein solution formulation wherein the protein is a gene recombinant protein.

The present invention provides said protein solution formulation wherein the protein is erythropoietin.

The present invention provides said protein solution formulation wherein the protein is granulocyte colony-stimulating factor.

The present invention provides said protein solution formulation wherein the protein is a protein having a sugar chain.

The present invention provides a method for stabilizing a protein solution formulation comprising storing said protein solution formulation filled in a container made from a hydrophobic resin at least in the part in contact with said formulation.

THE MOST PREFERRED EMBODIMENTS OF THE INVENTION

Suitable resins as container materials for use in the present invention include known medical container materials such as polyethylene (PE), polypropylene (PP), polyethylene terephthalate (PET), polycarbonate, polyethyl methcrylate, preferably resins represented by ring-opened polymers of cycloolefins such as norbornene or tetracyclododecene or derivatives thereof and hydrogenated products thereof; or copolymers having a cyclopentyl residue or substituted cyclopentyl residue inserted into the molecular chain by polymerization of a cycloolefin such as norbornene or tetracyclododecene or a derivative thereof and ethylene or propylene. Cycloolefins here include monocyclic and polycyclic compounds. Preferred are thermoplastic norbornene resines or thermoplastic tetracyclododecene resins. Thermoplastic norbornene resins include ring-opened polymers of norbornene monomers and hydrogenated products thereof, addition polymers of norbornene monomers, and addition polymers of norbornene monomers and olefins. Thermoplastic tetracyclododecene resins include ring-opened polymers of tetracyclododecene monomers and hydrogenated products thereof, addition polymers of tetracyclododecene monomers, and addition polymers of tetracyclododecene monomers and olefins. Thermoplastic norbornene resins are described in, for example, JPA No. 14882/91, JPA No. 122137/91 and JPA No. 63807/92.

Especially preferred are cycloolefin copolymers (COCs) such as copolymers of norbornene and an olefin such as ethylene, and copolymers of tetracyclododecene and an olefin such as ethylene. Cycloolefin polymers (COPs) obtained by ring-opening polymerization and hydrogenation of norbornene are also preferred. Such COCs and COPs are described in, for example, JPA No. 300939/93 or JPA No. 317411/93. Preferred structures of such COCs and COPs are shown below.

(1) Examples of COC (copolymers of tetracyclododecene and ethylene)

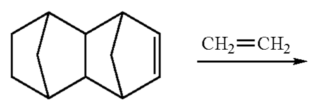

-continued

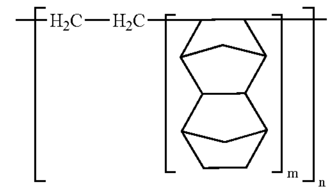

(2) Examples of COC (copolymers of norbornene and an olefin such as ethylene)

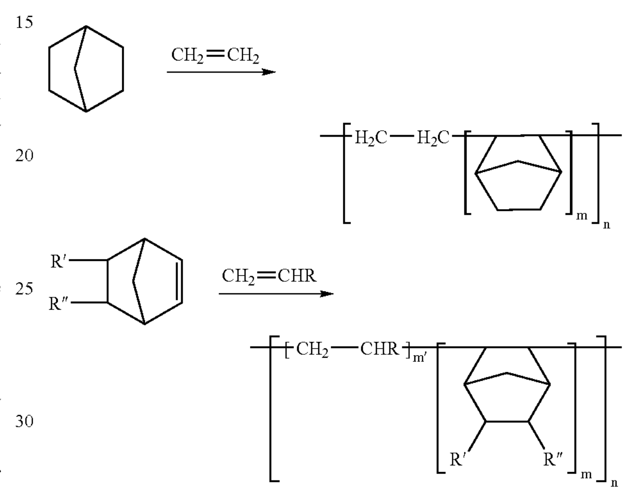

(3) Examples of COP (hydrogenated ring-opened polymers of norbornenes)

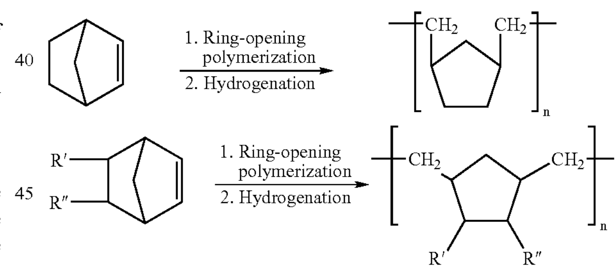

n: Polymerization degree; m, m': Molar ratio of copolymer content;

R: Lower alkyl group; R, R": Identical or different lower alkyl groups.

COCs are commercially available under, for example, Apel® from Mitsui Chemicals, and COPs are commercially available under, for example, Zeonex® or Zeonor® from Nippon Zeon or under Daikyo Resin CZ® from Daikyo Seiko.

COCs and COPs are the most preferred materials because they are characteristic of polyolefin resins which exhibit chemical properties such as resistance to heat and light and chemical resistance, while also being characteristic of amorphous resins in their physical properties such as mechanical properties, melt-flow characteristics and dimensional accuracy.

Protein solution formulations of the present invention refer to solution formulations containing a physiologically active protein prefilled in a container made from a hydrophobic resin at least for the part in direct contact with said formulations, whereby they can be stored for a long period.

The container in which protein solution formulations are filled according to the present invention can be selected depending on the purpose of use, and may be in a form having a defined volume such as vial, ampule, syringe or a large volume such as a bottle. The most preferable form is that of a syringe, especially a disposable syringe. Solutions are prefilled into such a syringe and supplied as prefilled syringe solution formulations, so as to prevent medical error and eliminate dissolution or suction of drug solutions, thereby providing rapid operation.

Physiologically active proteins used as active ingredients in the present invention include, but are not limited to, hematopoietic factors such as granulocyte colony-stimulating factor (G-CSF), granulocyte macrophage colony-stimulating factor (GM-CSF), erythropoietin (EPO) and trombopoietin; cytokines such as interferon, IL-1 and IL-6; monoclonal antibodies; tissue plasminogen activator (TPA); urokinase; serum albumin; blood coagulation factor VIII; leptin; insulin; and stem cell growth factor (SCF). Preferred proteins are hematopoietic factors such as EPO, G-CSF or trombopoietin and monoclonal antibodies, more preferably EPO, G-CSF and monoclonal antibodies.

Physiologically active proteins used as active ingredients in the present invention may be derived from natural sources or preferably obtained by genetic recombination so far as they have substantially the same biological activity as that of physiologically active proteins of mammals, especially human. Gene recombinant proteins may have the same amino acid sequence as that of natural proteins or may involve deletion, substitution or addition of one or more amino acids in said amino acid sequence while maintaining said biological activity. Physiologically active proteins may also be chemically modified with PEG or the like.

Especially preferred physiologically active proteins used as active ingredients in the present invention are proteins having a sugar chain. The sugar chain may be derived from any source, but preferably those added to mammalian cells. Mammalian cells include, for example, Chinese hamster ovary (CHO) cells, BHK cells, COS cells, human-derived cells, etc., among which CHO cells are most preferred.

When the physiologically active protein used as an active ingredient in the present invention is EPO, EPO may be prepared by any process, e.g. it may be extracted from human urine and isolated and purified by various techniques or may be produced by genetic engineering (see JPA No. 12288/86, for example) of Chinese hamster ovary (CHO) cells, BHK cells, COS cells, human-derived cells or the like and then extracted and isolated and purified by various techniques. EPO chemically modified with PEG or the like is also included (see International Publication WO90/12874). EPO having no sugar chain and chemically modified with PEG or the like is also included. EPO analogs are also included, in which EPO has been modified to increase the number of one or more glycosylation sites at the N-linked carbohydrate chain binding site or O-linked carbohydrate binding site in the amino acid sequence of EPO (see JPA No. 151398/96 and JPA No. 506023/96, for example) or the amount of sugar chains have been increased by increasing the content of sialic acid or the like without changing the number of sugar chain-binding sites.

When the physiologically active protein used as an active ingredient in the present invention is G-CSF, any high-purity human G-CSF can be used. G-CSF in the present invention may be prepared by any process, e.g., they may be extracted from cultures of a human tumor cell line and isolated and purified by various techniques or may be produced by genetic engineering in bacterial cells such as *E. coli*; yeast cells; animal culture cells such as Chinese hamster ovary (CHO), C127 or COS cells and then extracted and isolated and purified by various techniques. G-CSF is preferably produced by genetic recombination in *E. coli*, yeast or CHO cells, most preferably by genetic recombination in CHO cells. G-CSF chemically modified with PEG or the like is also included (see International Publication WO90/12874).

When the physiologically active protein used as an active ingredient in the present invention is a monoclonal antibody, the monoclonal antibody may be prepared by any process. Monoclonal antibodies can be basically constructed by known techniques as follows. An immunizing antigen is used to immunize a suitable host according to a standard immunization technique, and the resulting immunized cells are fused to known parent cells by a standard cell fusion technique, and then the fused cells are screened for monoclonal antibody-producing cells by a standard screening method. Monoclonal antibodies are not limited to those produced by hybridomas, but may also be chimeric antibodies having artificial modifications to lower heteroantigenicity to human or for other purposes. Reshaped humanized antibodies can also be used in the present invention, which are obtained by replacing the complementarity-determining regions of a human antibody by the complementarity-determining regions of an antibody derived from a non-human such as mouse by standard gene recombination techniques also known. These known techniques can be used to obtain reshaped humanized antibodies useful in the present invention.

Protein solution formulations of the present invention may contain diluents, solubilizing agents, isotonizing agents, excipients, pH-modifiers, soothing agents, buffers, sulfur-containing reducing agents, antioxidants or the like. For example, isotonizing agents include polyethylene glycol; and sugars such as dextran, mannitol, sorbitol, inositol, glucose, fructose, lactose, xylose, mannose, maltose, sucrose, raffinose. Surfur-containing reducing agents include N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms. Antioxidants include erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate, sodium metaphosphate. Other components commonly added to solution formulations may also be contained, e.g. inorganic salts such as sodium chloride, potassium chloride, calcium chloride, sodium phosphate, potassium phosphate, sodium bicarbonate; and organic salts such as sodium citrate, potassium citrate, sodium acetate.

Protein solution formulations of the present invention may further contain stabilizers suitable for various proteins including, but not limited to, surfactants (for example, nonionic surfactants such as sorbitan fatty acid esters, glycerin fatty acid esters, polyglycerin fatty acid esters, polyoxyethylene sorbitan fatty acid esters, polyoxyethylene sorbitol fatty acid esters, polyoxyethylene glycerin fatty acid esters, polyethylene glycol fatty acid esters, polyoxyethylene alkyl ethers, polyoxyethylene polyoxypropylene alkyl ethers, polyoxyethylene alkyl phenyl ethers, polyoxyethylene hardened castor oils, polyoxyethylene beeswax derivatives, polyoxyethylene lanolin derivatives, polyoxyethylene fatty acid amides; cationic surfactants such as alkyl sulfates, polyoxyethylene alkyl ether sulfates, alkyl sulfosuccinic acid ester salts; natural surfactants such as lecithin, glycerophospholipids, sphingophospholipids, sucrose fatty acid esters; especially preferred are polyoxyethylene sorbitan fatty acid esters, particularly polyoxyethylene sorbitan monooleate (Polysorbate 80) and polyoxyethylene sorbitan monolaurate (Polysorbate 20)), and amino acids such as D-, L- and DL-leucin, tryptophan, serine, glutamic acid, arginine, hystidine, lysine, methionine, phenylalanine and acetyltryptophan and salts thereof, preferably L-leucin, L-tryptophan, L-glutamic acid, L-arginine, L-hystidine and L-lysine and salts thereof.

Stable protein solution formulations of the present invention are normally administered via parenteral routes such as injection (subcutaneous or intravenous injection) or percutaneous, mucosal or nasal route, but may also be orally administered.

The amount of proteins contained in stable protein solution formulations of the present invention can be determined depending on the proteins used, the type of disease to be treated, the severity of the disease, the age of the patient and other factors.

Generally, proteins are contained in an amount of 0.01 µl-100 mg/ml, preferably 0.5 µl -50 mg/ml on the basis of the total amount of formulations of the present invention or injectable compositions after sugars have been added. For example, EPO is usually contained in solution formulations in an amount of 100-500,000 IU/ml (about 0.5-3000 µg/ml), preferably 200-100,000 IU/ml (about 1-600 µg/ml), more preferably 750-72,000 IU/ml (about 4-400 µg/ml). G-CSF is usually contained at a final dose concentration of 1-1000 µg/ml, preferably 10-800 µg/ml, more preferably 50-500 µg/ml. Antibodies are usually contained at a final dose concentration of 0.1-200 mg/ml, preferably 1 to 120 mg/ml.

Solution formulations of the present invention can be prepared by dissolving these components in an aqueous buffer known in the art of solution formulations such as phosphate and/or citrate buffers. Preferred phosphate buffers are sodium monohydrogen phosphate-sodium dihydrogen phosphate systems, and preferred citrate buffers are sodium citrate buffers.

When protein solution formulations of the present invention are erythropoietin solution formulations, they preferably contain EPO, a nonionic surfactant (such as Polysorbate 80, Polysorbate 20), an isotonizing agent (such as sodium chloride) and if desired, a stabilizer (such as an amino acid, preferably L-hystidine) at pH 5.0 8.0, preferably 5.5-7.0.

When protein solution formulations of the present invention are G-CSF solution formulations, they preferably contain G-CSF, a nonionic surfactant (such as Polysorbate 80, Polysorbate 20), and if desired, a diluent, solubilizing agent, isotonizing agent, excipient, pH-modifier, soothing agents, buffer, sulfur-containing reducing agent, antioxidant or the like at pH 5.0-8.0, preferably 6.0-7.0.

Stable protein solution formulations prefilled in a hydrophobic resin container of the present invention show very good EPO remaining levels as compared with glass containers even after an accelerated test at 40° C. for 6 months as demonstrated by testing on EPO and G-CSF in the examples below.

The present invention also provides a method for stabilizing a protein solution formulation comprising storing said protein solution formulation filled in a resin container as defined above. The term stabilization as used herein depends on the nature of the protein filled. In case of erythropoietin solution formulations, for example, it means that the remaining erythropoietin level is kept at 90% or more, preferably 95% or more, more preferably 98% or more after storage at 10° C. for 2 years or more or at 25° C. for 6 months or more, preferably one year or more, more preferably 2 years or more or at 400C for 2 weeks or more.

The present invention permits protein solution formulations to be stably stored at room temperatures for a long period.

INDUSTRIAL APPLICABILITY

Protein solution formulations prefilled in a hydrophobic resin container of the present invention show no or little loss in physiologically active protein content and are thus more stable than conventional solution formulations prefilled in a glass container. The present invention permits even protein solution formulations conventionally stored at low temperatures to be stored at room temperatures for a long period. Resin containers of the present invention have the advantage that they can be prepared by a simpler thermoforming process. Moreover, resin containers are well-suited to transportation because they are lighter and less fragile than glass containers, and therefore, the present invention is extremely industrially useful.

EXAMPLES

The following examples show the results of long-term stability testing and accelerated testing on erythropoietin (EPO) or granulocyte colony-stimulating factor (G-CSF) used as representative examples without, however, limiting the scope of the invention thereto. Various changes and modifications may be made by those skilled in the art.

In the following examples, evaluation of formulations was made by determining the content of EPO or G-CSF by RP-HPLC analysis.

Example 1

Long-term stability testing on EPO solution formulations stored at 10° C. and 25° C. Preparation of an EPO solution formulation A formulation containing the following components per 1 ml of the formulated solution was prepared and adjusted to pH 6.0 with 10 mM phosphate buffered saline.

| Component | Amount |
|---|---|
| EPO | 1500 IU |
| Polyoxyethylene sorbitan monooleate (Polysorbate 80) | 0.05 mg |
| Sodium chloride | 8.5 mg |
| L-histidine | 1.35 mg |

Test method

EPO solution formulations were prepared by filling 0.5 mL of the erythropoietin solution formulation prepared as described above into a glass container coated with silicone on the surface and a COP container (made from a COP, a hydrogenated ring-opened polymer of norbornene; Daikyo Resin CZ® manufactured by Daikyo Seiko), and subjected to stability testing at 10° C. for 3 months and 9 months and at 25° C. for 3 months, 6 months, 12 months and 24 months.

The EPO used in this example is a recombinant protein having a sugar chain produced in CHO cells.

The results (average of a triplicate test) are shown in Table 1 (storage at 10° C.) and Table 2 (storage at 25° C.) below. The values represent EPO contents determined by RP-HPLC analysis and the values in parentheses represent remaining levels expressed as percentages on the basis of the remaining levels at filling (initial) to 100%.

TABLE 1

Results of long-term stability testing at 10° C.

| Lot | Container material | Initial | 3 months | 9 months |
|---|---|---|---|---|
| 1 | Glass | 98.0% | 98.6% | 96.4% |
| | | (100.0%) | (100.6%) | (98.4%) |
| | COP | 98.0% | 98.7% | 97.1% |
| | | (100.0%) | (100.8%) | (99.0%) |
| 2 | Glass | 93.4% | 93.5% | 91.1% |
| | | (100.0%) | (100.2%) | (97.6%) |
| | COP | 92.7% | 94.2% | 92.0% |
| | | (100.0%) | (101.6%) | (99.3%) |
| 3 | Glass | 97.0% | 97.1% | 94.1% |
| | | (100.0%) | (100.0%) | (96.9%) |
| | COP | 96.7% | 97.8% | 95.7% |
| | | (100.0%) | (101.1%) | (99.0%) |

TABLE 2

Results of long-term stability testing at 25° C.

| Lot | Container material | Initial | 3 months | 6 months | 12 months | 24 months |
|---|---|---|---|---|---|---|
| 1 | Glass | 98.0% | 97.1% | 94.7% | 89.4% | 85.4% |
| | | (100.0%) | (99.0%) | (96.6%) | (91.4%) | (87.1%) |
| | COP | 98.0% | 98.8% | 98.1% | 97.2% | 96.2% |
| | | (100.0%) | (100.8%) | (100.1%) | (99.1%) | (98.2%) |
| 2 | Glass | 93.4% | 92.1% | 89.7% | 85.3% | 83.3% |
| | | (100.0%) | (98.6%) | (96.0%) | (91.4%) | (89.2%) |
| | COP | 92.7% | 93.7% | 92.9% | 91.7% | 89.4% |
| | | (100.0%) | (101.1%) | (100.2%) | (99.0%) | (96.4%) |
| 3 | Glass | 97.0% | 96.2% | 93.8% | 87.5% | 88.6% |
| | | (100.0%) | (99.2%) | (96.7%) | (90.2%) | (91.3%) |
| | COP | 96.7% | 98.1% | 97.5% | 96.3% | 94.9% |
| | | (100.0%) | (101.5%) | (100.8%) | (99.6%) | (98.1%) |

As shown from the tables above, remaining EPO levels in both glass and COP containers stored at 10° C. for 3 months and 9 months were maintained at approximately 100% of the initial levels. Remaining EPO levels in COP containers stored at 25° C. were maintained at 100% of the initial levels after for 3 months, 6 months and 12 months and at about 96-98% even after 24 months, in contrast to the tendency toward a slight decrease in glass containers.

These results confirmed that protein solution formulations, especially protein solution formulations having a sugar chain such as EPO prefilled in a resin container of the present invention show very high stability even after storage at room temperatures for a long period.

Example 2

Accelerated testing on EPO solution formulations at 40° C.

EPO solution formulations were prepared by filling a lass container and a COP container as described in Example 1 for storage under accelerated test conditions at 40° C. for 2 months, 4 months and 6 months.

The results (average of a triplicate test) are shown in Table 3 below.

TABLE 3

Results of accelerated testing at 40° C.

| Lot | Container material | Initial | 2 month | 4 months | 6 months |
|---|---|---|---|---|---|
| 1 | Glass | 98.0% | 84.2% | 79.8% | 72.3% |
| | | (100.0%) | (85.9%) | (81.4%) | (73.7%) |
| | COP | 98.0% | 94.9% | 92.8% | 87.5% |
| | | (100.0%) | (96.9%) | (94.7%) | (89.3%) |
| 2 | Glass | 93.4% | 83.6% | 79.4% | 67.1% |
| | | (100.0%) | (89.6%) | (85.1%) | (71.8%) |
| | COP | 92.7% | 89.6% | 86.1% | 81.2% |
| | | (100.0%) | (96.6%) | (92.9%) | (87.6%) |
| 3 | Glass | 97.0% | 88.8% | 82.8% | 73.1% |
| | | (100.0%) | (91.5%) | (85.3%) | (75.4%) |
| | COP | 96.7% | 92.8% | 88.7% | 85.7% |
| | | (100.0%) | (96.0%) | (91.8%) | (88.6%) |

These results show that EPO solution formulations filled in a COP container were more stable than those filled in a glass container at 40° C. for up to 6 months.

Example 3

Accelerated testing on EPO solution formulations at 50° C.

EPO solution formulations were prepared by filling a glass container and a COP container as described in Example 1 for storage under accelerated test conditions at 50° C. for one month, 2 months and 3 months, respectively.

The results (average of a triplicate test) are shown in Table 4 below.

TABLE 4

Results of accelerated testing at 50° C.

| Lot | Container material | Initial | 1 month | 2 months | 3 months |
|---|---|---|---|---|---|
| 1 | Glass | 98.0% | 68.5% | 48.4% | 34.5% |
| | | (100.0%) | (69.9%) | (49.4%) | (35.2%) |
| | COP | 98.0% | 81.6% | 65.9% | 55.5% |
| | | (100.0%) | (83.2%) | (67.3%) | (56.7%) |
| 2 | Glass | 93.4% | 60.2% | 45.2% | 33.4% |
| | | (100.0%) | (64.5%) | (48.4%) | (35.8%) |
| | COP | 92.7% | 77.3% | 62.6% | 52.3% |
| | | (100.0%) | (83.4%) | (67.5%) | (56.4%) |
| 3 | Glass | 97.0% | 65.6% | 46.8% | 28.6% |
| | | (100.0%) | (67.6%) | (48.3%) | (29.4%) |
| | COP | 96.7% | 79.4% | 65.0% | 55.2% |
| | | (100.0%) | (82.2%) | (67.3%) | (57.1%) |

Each of the three lots filled in both glass and COP containers showed an equal tendency towards a decrease in remaining levels under acceleration at 50° C., without any variation from lot to lot. In accelerated testing at 50° C. for up to 3 months, EPO solution formulations filled in a COP container were more stable than those filled in a glass container.

Example 4

Accelerated Testing on EPO Solution Formulations at 60° C.

EPO solution formulations were prepared by filling a glass container and a COP container as described in Example 1 and for storage under accelerated test conditions at 60° C. for one week, 2 weeks and 3 weeks, respectively.

The results (average of a triplicate test) are shown in Table 5 below.

TABLE 5

Results of accelerated testing at 60° C.

| Lot | Container material | Initial | 1 week | 2 weeks | 3 weeks |
|---|---|---|---|---|---|
| 1 | Glass | 98.0% (100.0%) | 80.1% (81.7%) | 70.2% (71.6%) | 55.9% (57.0%) |
| | COP | 98.0% (100.0%) | 87.9% (89.7%) | 80.4% (82.0%) | 73.2% (74.7%) |
| 2 | Glass | 93.4% (100.0%) | 74.5% (79.8%) | 65.6% (70.3%) | 51.7% (55.4%) |
| | COP | 92.7% (100.0%) | 83.0% (89.5%) | 75.6% (81.5%) | 68.5% (73.9%) |
| 3 | Glass | 97.0% (100.0%) | 79.5% (81.9%) | 65.1% (67.1%) | 54.4% (56.1%) |
| | COP | 96.7% (100.0%) | 86.1% (89.0%) | 78.4% (81.1%) | 68.6% (70.9%) |

Each of the three lots filled in both glass and COP containers showed an equal tendency towards a decrease in remaining levels under acceleration at 60° C., without any variation from lot to lot. In accelerated testing at 60° C. for up to 3 months, EPO solution formulations filled in a COP container were more stable than those filled in a glass container.

Example 5

Accelerated testing on G-CSF solution formulations at 40° C. Preparation of a G-CSF solution formulation A formulation containing the following components per 1 ml of the formulated solution was prepared and adjusted to pH 6.5 with 1 mol/L hydrochloric acid.

| | |
|---|---|
| G-CSF | 125 μg |
| Polyoxyethylene sorbitan monooleate (Polysorbate 20) | 0.1 mg |
| Sodium chloride | 7.5 mg |

Test method

G-CSF solution formulations were prepared by filling 0.5 mL of the G-CSF solution formulation prepared as described above in a glass container uncoated with silicone on the surface, a glass container coated with silicone on the surface and a COP container (made from a COP, a hydrogenated ring-opened polymer of norbornene; Daikyo Resin CZ® manufactured by Daikyo Seiko), and stored under accelerated test conditions at 40° C. for 2 weeks.

The G-CSF used in this example is a recombinant protein having a sugar chain produced in CHO cells.

The results (average of a triplicate test) are shown in Table 6 below. The values represent G-CSF contents determined by RP-HPLC analysis and the values in parentheses represent remaining levels expressed as percentages on the basis of the remaining levels at filling (initial) to 100%.

TABLE 6

Results of accelerated testing at 40° C.

| Container material | Initial | 2 weeks |
|---|---|---|
| Glass (uncoated with silicone oil) | 100.1% (100.0%) | 85.4% (85.3%) |
| Glass (coated with silicone oil) | 100.1% (100.0%) | 84.8% (84.7%) |
| COP | 100.1% (100.0%) | 94.6% (94.5%) |

Remaining levels as compared with the initial levels were 85.4% (uncoated with silicone oil) and 84.8% (coated with silicone oil) in glass containers in contrast to 94.6% in COP containers. These results show that G-CSF solution formulations filled in a COP container were more stable than those filled in a glass container at 40° C. for up to 2 weeks.

Example 6

Impurities-leaching test and adsorption test to containers

An erythropoietin solution formulation containing 1500 IU or 48000 IU of EPO per 1 ml of the formulated solution was prepared. The formulation containing 1500 IU was prepared as described in Example 1. The formulation containing 48000 IU was prepared as follows.

A formulation containing the following components per 1 ml of the formulated solution was prepared and adjusted to pH 6.0 with 25 mM phosphate buffered saline.

| | |
|---|---|
| EPO | 48000 IU |
| Polyoxyethylene sorbitan monooleate (Polysorbate 80) | 0.05 mg |
| Sodium chloride | 7.0 mg |
| L-histidine | 1.35 mg |

EPO solution formulations were prepared by filling 0.5 mL of the formulation prepared as described above into a glass syringe coated with silicone on the surface, a COP syringe, a COP vial (both made from a COP, a hydrogenated ring-opened polymer of norbornene; Daikyo Resin CZ® manufactured by Daikyo Seiko), a glass ampule uncoated with silicone on the surface and a glass vial uncoated with silicone on the surface.

Impurities-Leaching Test

Evaluation was made to determine whether or not any peak of impurities leached from each container other than the peak of EPO is observed when remaining levels in EPO solution formulations prepared in various containers were assayed. No peak of impurities was observed in any of the samples, which confirmed that no impurities were leached from containers.

Adsorption Test to Containers

EPO in each container was recovered and the recovery (%) based on the formulated EPO solution was determined. The results (average of a triplicate test) are shown in Table 7.

TABLE 7

Recovery based on the formulated solution

| | 1500 IU | 48,000 IU |
|---|---|---|
| Glass syringe (coated with silicone oil) | 98.7% | 99.7% |
| COP syringe | 99.3% | 99.6% |
| COP vial | 99.6% | 100.0% |
| Glass ampule (uncoated with silicone oil) | 93.6% | 99.7% |
| Glass vial (uncoated with silicone oil) | 94.1% | — |

EPO prepared in COP containers showed a recovery comparable to or higher than that of EPO prepared in a glass container coated with silicone oil and much higher than that obtained in glass containers uncoated with silicone oil. Thus, COP containers exhibited superior characteristics as containers with less adsorption to container walls being observed.

Example 7

Long-term stability testing and accelerated testing on EPO solution formulations in various resin containers EPO solution formulations were prepared by filling 0.5 mL of an erythropoietin solution formulation containing 1500 IU EPO per 1 ml of the formulated solution (prepared as described in Example 1) into a glass container, a COP container (made from a COP, a hydrogenated ring-opened polymer of norbornene; Daikyo Resin CZ® manufactured by Daikyo Seiko), and a COC container (a copolymer of tetracyclododecene and an olefin such as ethylene: Apel® manufactured by Mitsui Chemicals).

Thus prepared EPO solution formulations were subjected to (1) stability testing at 25° C. for 2 months, 3 months and 6 months, and EPO solution formulations filled in glass and COC containers were further subjected to (2) accelerated testing at 40° C. for 2 months, 4 months and 6 months, (3) accelerated testing at 50° C. for 1 month, 2 months and 3 months, and (4) accelerated testing at 60° C. for 1 week, 2 weeks and 3 weeks. The results (average of a triplicate test) are shown in Tables 8, 9, 10 and 11 below, respectively. The values represent remaining levels expressed as percentages on the basis of the remaining levels at filling (initial) to 100%.

TABLE 8

Results of log-term stability testing at 25° C.

| Container | 2 months | 3 months | 6 months |
|---|---|---|---|
| Glass vial | 97.4% | 97.8% | 95.1% |
| COP vial | 100.2% | 99.9% | 99.9% |
| COC vial | 100.1% | 100.2% | 100.1% |

TABLE 9

Results of accelerated testing at 40° C.

| Container | 2 months | 4 months | 6 months |
|---|---|---|---|
| Glass vial | 86.7% | 68.2% | 43.5% |
| COC vial | 96.8% | 87.6% | 83.1% |

TABLE 10

Results of accelerated testing at 50° C.

| Container | 1 month | 2 months | 3 months |
|---|---|---|---|
| Glass vial | 62.5% | 41.4% | 24.0% |
| COC vial | 84.9% | 71.8% | 57.9% |

TABLE 11

Results of accelerated testing at 60° C.

| Container | 1 week | 2 weeks | 3 weeks |
|---|---|---|---|
| Glass vial | 69.7% | 50.3% | 32.9% |
| COC vial | 82.2% | 69.5% | 57.8% |

In all the tests, EPO solution formulations prepared in resin containers showed higher remaining levels than those prepared in glass containers.

What is claimed is:

1. A stable protein solution formulation filled in a syringe made from a hydrophobic resin at least for the part in direct contact with said formulation, wherein the protein solution formulation is a prefilled syringe solution formulation and can be stored at room temperature in said syringe, wherein the protein is recombinant erythropoietin or granulocyte colony-stimulation factor, and wherein said hydrophobic resin is selected from the group consisting of a thermoplastic norbornene resin and a thermoplastic tetracyclododecene resin.

2. A stable protein solution formulation filled in a syringe made from a hydrophobic resin, wherein the protein solution formulation is a prefilled syringe solution formulation and can be stored at room temperature in said syringe, wherein the protein is recombinant erythropoietin or granulocyte colony-stimulation factor, and wherein said hydrophobic resin is selected from the group consisting of a thermoplastic norbornene resin and a thermoplastic tetracyclododecene resin.

3. The protein solution formulation of claim 1 wherein the thermoplastic norbornene resin comprises a ring-opened polymer of norbornene and the thermoplastic tetracyclododecene resin comprises a ring-opened polymer of tetracyclododecene.

4. The protein solution formulation of claim 1 wherein the thermoplastic norbornene resin comprises a hydrogenated ring-opened polymer of norbornene and the thermoplastic tetracyclododecene resin comprises a hydrogenated ring-opened polymer of tetracyclododecene.

5. The protein solution formulation of claim 1 wherein the thermoplastic norbornene resin comprises a copolymer of norbornene or a derivative thereof and ethylene or propylene, and the thermoplastic tetracyclododecene resin comprises a copolymer of tetracyclododecene or a derivative thereof and ethylene or propylene.

6. The protein solution formulation of claim 5 wherein the thermoplastic norbornene resin comprises a copolymer of norbornene and ethylene, and the thermoplastic tetracyclododecene resin comprises a copolymer of tetracyclododecene and ethylene.

7. A stable protein solution formulation filled in a syringe made from a hydrophobic resin at least for the part in direct contact with said formulation, wherein the protein solution formulation is a prefilled syringe solution formulation and can be stored at room temperature in said syringe, wherein the protein is recombinant erythropoietin or granulocyte colony-stimulation factor, and wherein said hydrophobic resin is selected from the group consisting of a thermoplastic norbornene resin and a thermoplastic tetracyclododecene resin, and wherein the protein is a protein having a sugar chain.

8. The protein solution formulation of claims 1 or 2, which is optionally stored at room temperatures.

9. A method for preparing a protein solution formulation for delivery, wherein said method comprises filling said protein solution formulation in a syringe made from a hydrophobic resin at least for the part in direct contact with said formulation, wherein the protein solution formulation is a prefilled syringe solution formulation and can be stored at room temperature in said syringe, wherein the protein is recombinant erythopoietin or granulocyte colony-stimulating factor, and wherein said hydrophobic resin is selected from the group consisting of a thermoplastic norbornene resin and a thermoplastic tetracylododecene resin.

10. A method for preparing a protein solution formulation for delivery, wherein said method comprises filling a syringe made from a hydrophobic resin with a protein solution formulation, wherein said protein solution formulation is a prefilled syringe solution formulation and can be stored at room temperature in said syringe, wherein the protein is recombinant erythropoietin or granulocyte colony-stimulation factor, and wherein said hydrophobic resin is selected from the group consisting of a thermoplastic norbornene resin and a thermoplastic tetracyclododecene resin.

* * * * *

UNITED STATES PATENT AND TRADEMARK OFFICE

CERTIFICATE OF CORRECTION

PATENT NO. : 7,253,142 B1
APPLICATION NO. : 09/720757
DATED : August 7, 2007
INVENTOR(S) : Nobuyuki Suzuki et al.

It is certified that error appears in the above-identified patent and that said Letters Patent is hereby corrected as shown below:

On The Title Page
Item (30), Foreign Application Priority Data: the foreign priority date "August 9, 1999" should be --September 8, 1999--.

Signed and Sealed this

Twenty-third Day of October, 2007

JON W. DUDAS
*Director of the United States Patent and Trademark Office*